(12) United States Patent
Mizukami et al.

(10) Patent No.: US 7,767,409 B2
(45) Date of Patent: Aug. 3, 2010

(54) METHOD FOR DETECTION OF SUBSTANCE BOUND TO NUCLEAR RECEPTOR

(75) Inventors: Haruki Mizukami, Tokyo (JP); Akira Okuyama, Tokyo (JP); Yasuhiko Hatano, Tokyo (JP)

(73) Assignee: Fujikura Kasei Co., Ltd., Tokyo (JP)

( * ) Notice: Subject to any disclaimer, the term of this patent is extended or adjusted under 35 U.S.C. 154(b) by 183 days.

(21) Appl. No.: 11/887,477

(22) PCT Filed: Dec. 13, 2005

(86) PCT No.: PCT/JP2005/022846
§ 371 (c)(1),
(2), (4) Date: Feb. 20, 2008

(87) PCT Pub. No.: WO2006/103813
PCT Pub. Date: Oct. 5, 2006

(65) Prior Publication Data
US 2008/0213799 A1  Sep. 4, 2008

(30) Foreign Application Priority Data
Mar. 29, 2005  (JP)  ............................. 2005-093876

(51) Int. Cl.
*G01N 33/53* (2006.01)
(52) U.S. Cl. ....................................... 435/7.2
(58) Field of Classification Search ................. None
See application file for complete search history.

(56) References Cited

FOREIGN PATENT DOCUMENTS

| JP | A 2002-48794 | 2/2002 |
| WO | WO 99/50664 | 10/1999 |
| WO | WO 00/40965 A | 7/2000 |

OTHER PUBLICATIONS

Chen, Hongwu et al. "Regulation of Hormone-Induced Histone Hyperacetylation and Gene Activation via Acetylation of an Acetylase." *Cell.* vol. 98, pp. 675-686, Sep. 3, 1999.

Kamei, Yasutomi et al. "A CBP Integrator Complex Mediates Transcriptional Activation and AP-1 Inhibition by Nuclear Receptors." *Cell.* vol. 85, pp. 403-414, May 3, 1996.

Le Douarin, Bertrand et al. "The N-terminal part of TIF1, a putative mediator of the ligand-dependent activation function (AF-2) of nuclear receptors, is fused to B-raf in the oncogenic protein T18." *The EMBO Journal.* vol. 14, No. 9, pp. 2020-2033, 1995.

Voegel, Johannes et al. "TIF2, a 160 kDa transcriptional mediator for the ligand-dependent activation function AF-2 of nuclear receptors." *The EMBO Journal.* vol. 15, No. 14, pp. 3667-3675, 1996.

Cavailles, Vincent et al. "Nuclear factor RIP140 modulates transcriptional activation by the estrogen receptor." *The EMBO Journal.* vol. 14, No. 15, pp. 3741-3751, 1995.

Cowley, Shaun et al. "Estrogen Receptors α and β Form Heterodimers on DNA." *The Journal of Biological Chemistry.* vol. 272, No. 32, pp. 19858-19862, Aug. 8, 1997.

Harringotn, William et al. "Activities of estrogen receptor alpha- and beta-selective ligands at diverse estrogen responsive gene sites mediating transactivation or transrepression." *Molecular and Cellular Endocrinology 206.* pp. 13-22, 2003.

Okuyama, Akira et al. "Development of Estrogen Receptor/Coactivator, Ligand Assay." 7th *Annual Meeting of Japan Society of Endocrine Disrupters Research.* p. 208, Dec. 2004.

Mizukami, Haruki. "Project of Research and Development of New Technology Corresponding to problems of 2003" pp. 90-93, Feb. 2004.

Makoto Makishima et al., "Identification of a Nuclear Receptor for Bile Acids," 284 Science (May 21, 1999).

Jun-ichi Nishikawa et al., "New Screening Methods for Chemicals with Hormonal Activities Using Interaction of Nuclear Hormone Receptor with Coactivator," 154 Toxicology and Applied Pharmacy 1, (Jan. 1, 1999).

*Primary Examiner*—Michael Pak
(74) *Attorney, Agent, or Firm*—Oliff & Berridge, PLC

(57) ABSTRACT

Provided is a detection method including exposing, to contact with a surface to which a cofactor has been bound, a nuclear receptor protein serving as a counterpart of the cofactor and a test sample; and detecting a substance which is contained in the test sample and which binds to the nuclear receptor, on the basis of a change in degree of binding between the nuclear receptor protein and the cofactor. The detection method is means for detecting a living-body-related substance, which means employs a nuclear receptor-cofactor system, exhibits detection high sensitivity, provides a convenient detection process, and realizes efficient establishment of a detection system.

6 Claims, 6 Drawing Sheets

Fig. 5

| Day | General assay method (preparation of five kits) | | | | | Day | Novel preparation method (preparation of 50 kits) |
|---|---|---|---|---|---|---|---|
| | 1st | 2nd | 3rd | 4th | 5th | | |
| Production capacity | | | | | | | 50 kits |
| Placement of order | 1 kit | 2 kits | | | | 0 | · Checking of materials<br>· Reagent preparation (agar plate) |
| 1 | · Checking of materials<br>· Reagent preparation (agar plate) | | | | | 1 | Plate culture |
| 2 | Plate culture<br>Small scale culture | | | | | 2 | Small scale culture |
| 3 | Large scale culture (1L) | Small scale | | | | 3 | Large scale culture |
| 4 | · Purification<br>· SDS-PAGE<br>· Coating of plate for checking activity | Large scale | Small scale | | | 4 | · Purification<br>· ER concentration determination test (SRC1 concentration determination test)<br>· Initiation of lyophilization |
| 5 | Plate blocking | | Large scale | Small scale | | 5 | · SDS-PAGE<br>· Reagent preparation, dispensing |
| 6 | · Checking activity (determination of coating amount)<br>· Coating of production plate | | | Large scale | Small scale culture | 6 | · Reagent preparation, dispensing |
| 7 | Plate blocking | | | | Large scale culture | 7 | · Quality control test |
| 8 | · Quality control test<br>· Plate drying | | | | · Purification<br>· SDS-PAGE<br>· Coating of plate for checking activity | 8 | |
| 9 | · Reagent preparation<br>· Product quality control test | | | | Plate blocking | 9 | |
| 10 | | | | | · Checking activity (determination of coating amount)<br>· Coating of production plate | 10 | |
| 11 | | | | | Plate blocking | 11 | |
| 12 | | | | | · Quality control test<br>· Plate drying | 12 | |
| 13 | | | | | · Reagent preparation<br>· Product quality control test | 13 | |
| 14 | | | | | | 14 | |

Fig. 8
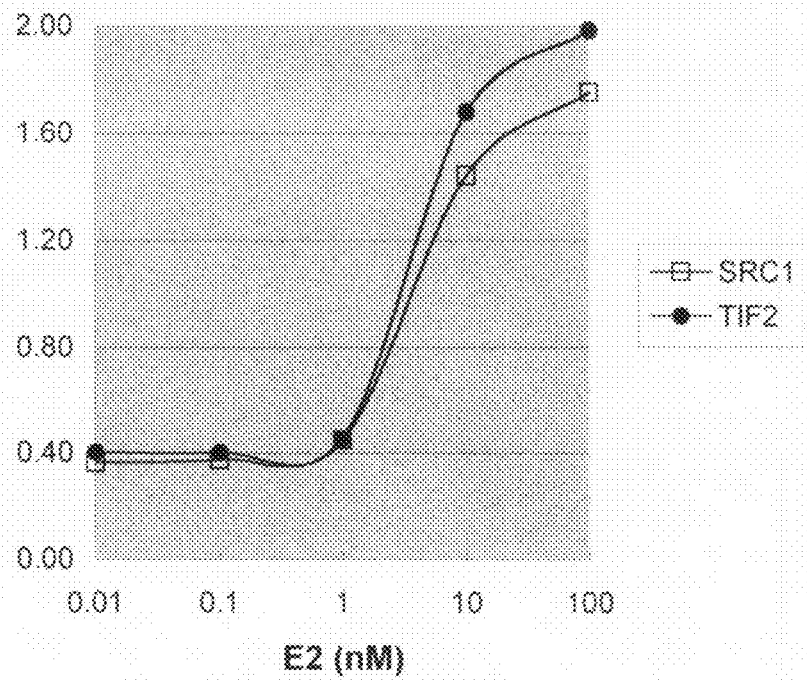
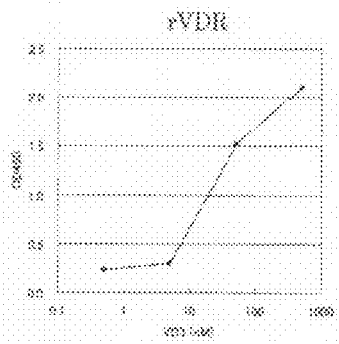
Fig. 9A
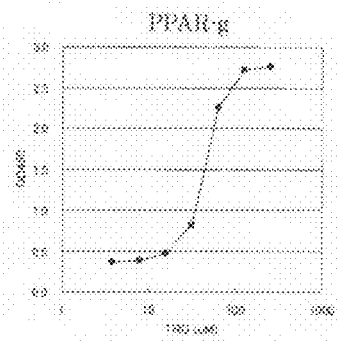
Fig. 9B
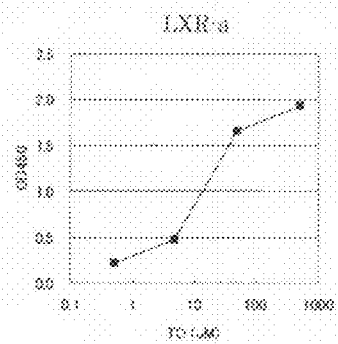
Fig. 9C
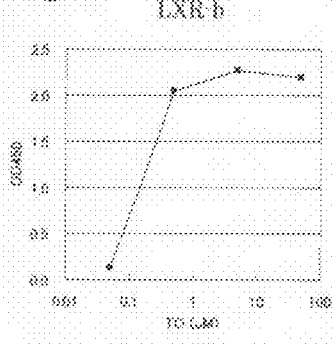
Fig. 9D
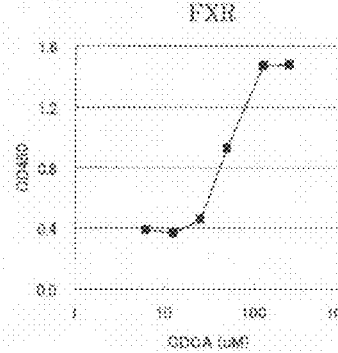
Fig. 9E

METHOD FOR DETECTION OF SUBSTANCE BOUND TO NUCLEAR RECEPTOR

TECHNICAL FIELD

The present invention relates to a method for detecting a living-body-related substance. More particularly, the present invention relates to a method for detecting, for example, an agonist, an antagonist, or a modulator for a nuclear receptor.

BACKGROUND ART

Nuclear receptors have become of interest as important key substances for drug discovery. Specifically, screening studies using nuclear receptors have elucidated that tamoxifen, which exhibits an antagonistic effect on an estrogen receptor, is effective as a breast cancer therapeutic agent. However, tamoxifen has been elucidated to exacerbate uterine cancer. It has been suggested that such different effects of a drug which acts on a single nuclear receptor are strongly associated with cofactors of the nuclear receptor.

Conventionally, screening methods for drug discovery using nuclear receptors as key substances have generally employed a receptor binding assay which detects binding of a ligand to a receptor. The detection principle of such a receptor binding assay generally involves, as an index, competitive inhibition of hormone receptor binding of a labeled hormone and a target chemical substance having affinity to the hormone receptor. This method is advantageous for rapid screening of numerous drug candidates. However, although this method can determine the degree of binding of a chemical substance to a receptor, the method encounters difficulty in determining physiological effects of the chemical substance on the receptor; for example, whether the chemical substance exhibits an agonistic effect or an antagonistic effect on the receptor.

Recent studies on such receptors have elucidated that physiological effects of a ligand are strongly dictated by cofactors. Under such circumstances, there has been recognized the utility of a screening system employing cells, such as a reporter gene assay or a two-hybrid assay. However, such an assay, which employs cells, involves problems in that, for example, a culturing apparatus is required; cell culturing requires an intricate process; cell manipulation requires skill to some extent; and a long period of time is required for the assay since cell growth is a rate-determining step in the assay. Therefore, such an assay may be inappropriate as a screening technique for drug discovery requiring rapid screening of numerous samples.

In view of the foregoing, an important key for drug discovery and development is establishment of an in vitro screening system capable of rapidly and conveniently assaying numerous samples on the basis of their mechanisms of physiological action.

Hitherto, forty-eight human nuclear receptors have been known. These include many receptors whose functions have not yet been elucidated (so-called orphan nuclear receptors), and they are considered to play important biological roles. As has been found, several cofactors which act, in conjunction with a receptor, on expression of a specific gene are common to the receptor irrespective of the type of the receptor. As has also been found, the receptor binds to a different type of cofactor depending on the type of a ligand (i.e., an agonist, an antagonist, or a modulator), and the cofactor is involved in expression of a specific gene. When these findings are put into perspective where physiological action of orphan receptors and the relation between cofactors-receptors interaction (combination) and physiological functions (pathological conditions) have been scientifically elucidated, a crucial point in the development of a screening method useful for drug discovery employing a nuclear receptor as a key substance is to establish a high-throughput screening system for drug discovery as soon as possible. Such a screening system must take into consideration contribution of a plurality of different cofactors.

In general, a conventional cofactor-containing receptor-ligand assay system employs a technique similar to that employed in enzyme-linked immunosorbent assay (hereinafter abbreviated as "ELISA"), which is an assay system using an antibody. Conceivably, such a conventional receptor-ligand assay system is established in a manner similar to that in the case of ELISA. Establishment of an assay system based on ELISA requires a long period of time for preparation of a necessary anti-receptor antibody, and also requires selection of assay conditions; for example, selection of conditions for immobilization on a microwell plate, or selection of detection means (use of the fluorescence method or a radioactive substance). Since a variety of nuclear receptor-cofactor combinations are provided, when an assay system is established for each of the combinations as in the case of the aforementioned conventional assay system, a large number of assay systems are required, which is not efficient.

Therefore, an object of the present invention is to provide means for detecting a living-body-related substance, which means employs a nuclear receptor-cofactor system, exhibits high detection sensitivity, provides a convenient detection process, and realizes efficient establishment of a detection system.

DISCLOSURE OF THE INVENTION

The present inventors have found that the aforementioned object can be achieved by establishing the following assay system. The present invention has been accomplished on the basis of this finding.

Accordingly, the present invention provides a detection method comprising exposing, to a surface to which a cofactor has been bound, a nuclear receptor protein serving as a counterpart of the cofactor and a test sample; and detecting a substance which is contained in the test sample and which binds to the nuclear receptor, on the basis of a change in degree of binding between the nuclear receptor protein and the cofactor (hereinafter the detection method may be referred to as "the present detection method").

[Nuclear Receptor and Cofactor]

The nuclear receptor, which is an essential element in the present detection method, is known as, for example, a steroid hormone receptor, and is known to be present in cytoplasm or nucleus. As has been known, when a ligand binds to a nuclear receptor, the nuclear receptor binds to a specific gene region, thereby activating various genes. Specific examples of known nuclear receptors include estrogen receptor α (M12674), estrogen receptor β (AB006590), androgen receptor (M20132), progesterone receptor (M15716), glucocorticoid receptor (M10901), mineralcorticoid receptor (M16801), retinoic acid receptor α (X06614), retinoic acid receptor β (X07282), retinoic acid receptor γ (M24857), thyroid hormone receptor α (Y00479), thyroid hormone receptor β (X04707), vitamin D receptor (J03258), retinoid X receptor α (X52773), retinoid X receptor β (M84820), retinoid X receptor γ (U38480), peroxisome proliferator-activated receptor α (L02932), peroxisome proliferator-activated receptor γ (U79012), peroxisome proliferator-activated receptor δ

(L07592), liver X receptor α (U22662), liver X receptor β (U07132), farnesol X receptor (U68233), steroid and xenobiotic receptor (AY091855), constitutive androstane receptor (L29263), Rev-Erb A receptor α (X53327), Rev-Erb A receptor β (D16815), RAR-related orphan receptor α (U04898), RAR-related orphan receptor β (Y08639), RAR-related orphan receptor γ (U16997), hepatocyte nuclear factor 4α (X76930), hepatocyte nuclear factor 4γ (Z49826), testicular orphan receptor 2 (M29960), testicular orphan receptor 4 (L27586), chicken ovalbumin upstream promoter transcription factor I (NM_005654), chicken ovalbumin upstream promoter transcription factor II (NM_021005), chicken ovalbumin upstream promoter transcription factor γ (X12794), estrogen-related receptor α (X51416), estrogen-related receptor β (X51417), estrogen-related receptor γ (AF094518), nerve growth factor-inducible gene Bα (L13740), nerve growth factor-inducible gene Bβ (X75918), nerve growth factor-inducible gene Bγ (D38530), germ cell nuclear factor (U80802), steroidogenic factor 1 (U76388), liver receptor homologous protein (U93553), photoreceptor cell-specific nuclear receptor (AF121129), *Drosophila tailless* gene receptor human homologue (AF220532), small heterodimer partner protein (L76571), and dosage-sensitive sex reversal-AHC critical region on the X chromosome gene 1 (U31929) (each of the aforementioned parenthesized numbers is GenBank Accession No. representing a gene sequence encoding the corresponding nuclear receptor, or an amino acid sequence of the nuclear receptor).

The cofactor is an intracellular transcription factor which regulates gene transcription associated with the aforementioned nuclear receptors. As has been known, generally, when a ligand binds to a nuclear receptor, the nuclear receptor undergoes structural change, and a cofactor binds to the nuclear receptor, whereby a specific target gene is regulated. As described above, a nuclear receptor and a cofactor are not necessarily in one-to-one correspondence. For example, it is known that, depending on the type of a ligand which binds to a nuclear receptor, the nuclear receptor may bind to different cofactors. It is also known that different nuclear receptors may bind to a common cofactor. The cofactors are roughly classified into a coactivator (i.e., a cofactor which, when an agonist binds to a nuclear receptor, binds to the nuclear receptor, to thereby promote gene transcription); and a corepressor (i.e., a cofactor which, when an antagonist binds to a nuclear receptor, binds to the nuclear receptor, to thereby suppress gene transcription).

Examples of cofactors which have hitherto been known include, but are not limited to, ACTR (activator of thyroid and retinoic acid receptors) (Chen H, et al.: Cell September 3; 98 (5): 675-686 (1999)), SRC (steroid receptor coactivator) 1 (Kamei, et al.: Cell 85, 403-414 (1996)), TIF (transcriptional intermediate factor) 1 (Le Douarin, B., et al.: EMBO J. 14, 2020-2033 (1995)), TIF2 (Voe gel, J. J., et al.: EMBO J. 15, (1996)), and RIP140 (receptor interacting protein) (Cavailles, V., et al.: EMBO J. 14, 3741-3751 (1995)).

A nuclear receptor or cofactor employed in the present detection method is preferably a recombinant protein produced through a protein engineering technique.

Such a recombinant protein may be produced through a known technique. Specifically, a nuclear receptor or cofactor of interest can be produced through the following procedure: a gene amplification primer is produced on the basis of the disclosed entire or partial gene or amino acid sequence; a gene product encoding the nuclear receptor or cofactor of interest is amplified by use of the gene amplification primer through a gene amplification technique (e.g., PCR or RT-PCR); the thus-amplified gene product is inserted into a known gene vector; and the vector is introduced into a host cell for expression of the gene. The thus-produced nuclear receptor or cofactor may be the entirety of a naturally occurring nuclear receptor or cofactor protein, or may be a portion thereof so long as an intrinsically acting portion is retained (as used herein, the term "nuclear receptor" refers to the entirety or a portion of a naturally occurring nuclear receptor, and the term "cofactor" refers to the entirety of a portion or a naturally occurring cofactor).

The aforementioned recombinant protein or peptide is preferably expressed as a fusion protein with a known protein. Particularly, a nuclear receptor protein employed in the present detection method is preferably expressed as a fusion protein.

Examples of the aforementioned known protein (hereinafter may be referred to as a "tag protein") include, but are not limited to, glutathione S-transferase (GST), maltose-binding protein (MBP), thioredoxin (TRX), β-galactosidase (βgal), histidine tag (His-Tag), Myc epitope (Myc), hemagglutinin epitope (HA), T7 epitope, HSV epitope, FLAG, Xpress, and GFP.

Such a fusion protein may be produced through a known method. Specifically, a fusion protein of interest can be produced through, for example, the following procedure: a gene encoding the entirety or a portion of a nuclear receptor protein or a cofactor is inserted into a gene expression vector; a gene encoding any of the aforementioned tag proteins is inserted into the vector at a site upstream or downstream of the above-inserted main gene; and the nucleotide sequence of a promoter or a portion where the genes encoding both of the proteins are fused is designed so that these proteins are expressed as a continuous fusion protein. A tag-protein-fused protein expression vector employed may be a commercially available one [e.g., pGEX (product of Amersham Bioscience) or pET (product of Novagen)].

[Surface on which the Present Detection Method is Performed]

No particular limitation is imposed on the material or form of a "surface," so long as a cofactor can be bound to the surface. The surface material employed may be a variety of materials, including glass, plastic, and metal. No particular limitation is imposed on the surface form, and the surface form may be, for example, a flat or concave form. In general, the surface form is preferably a concave form. More specifically, the present detection method is particularly preferably performed on a microwell plate.

Specifically, a microwell plate has, at a surface thereof, numerous wells, in which the present detection method, which employs combination of the same or different types of cofactors and a nuclear receptor protein(s), can be carried out efficiently. Particularly when the present detection method employs two or more nuclear receptor proteins and cofactors serving as counterparts of the respective proteins, and the detection method is performed in different respective wells of a single microwell plate, to thereby collectively detect substances which are contained in a test sample and which bind to the two or more nuclear receptors, efficient search of target substances, which is an object of the present invention, can be attained.

Means for binding a cofactor to a surface is preferably a biological method or a chemical method.

In a biological method, a cofactor is bound to a surface by the mediation of a living-body-related substance, whereas in a chemical method, a cofactor is bound to a surface by use of a chemically produced bond-forming chain. Preferably, the former method (i.e., a biological method) is employed.

The bond-forming chain employed in a chemical method may be, for example, covalent bond or coordination bond. In the case where covalent bond is employed, preferably, a covalent-bond-forming chain molecule has, at both ends thereof, a functional group which can bind to a surface material or a cofactor (protein) through reaction (e.g., an amino group, a carboxyl group, or a thiol group). In the case where coordination bond is employed, preferably, a chelate molecule (e.g., a nickel chelate molecule) is provided on a surface, and an element which can bind to the chelate through reaction (e.g., a His-tag) is introduced into a cofactor during expression of the cofactor (recombinant).

Examples of the living-body-related substance employed in a biological method include antibodies, enzymes, and binding proteins (e.g., avidin and streptavidin). Particularly preferably, avidin or streptavidin, which is a biotin-specific binding protein, is employed.

Specifically, preferably, a surface coated with avidin or streptavidin (i.e., an avidin-immobilized surface) is exposed to a cofactor to which biotin (i.e., a binding protein specific to avidin or streptavidin) has been bound, to thereby form a cofactor-bound surface through avidin-biotin binding. A method for preparing an avidin-immobilized surface by fixing avidin or streptavidin onto a surface, and a method for binding biotin to a cofactor (protein or peptide) are known and convenient (such methods will be specifically exemplified in the Examples hereinbelow).

As described above, a cofactor-bound surface may be formed by use of an antibody as a cofactor-binding molecule. In such a case, an antibody to a cofactor (the antibody may be a monoclonal or polyclonal antibody) may be immobilized on a surface. However, as described above, at present, immobilization of an antibody on a tag protein fused with a cofactor (many anti-tag protein antibodies are commercially available) realizes establishment of a detection system conveniently as compared with the case where an anti-cofactor antibody, which must be produced upon use, is employed.

A cofactor-bound surface may also be formed by use of an enzyme as a cofactor-binding molecule. In this case, a cofactor can be fixed, via an enzyme of interest, onto a surface by use of a fusion protein of the cofactor and an enzyme protein (e.g., GST or MBP) serving as a tag protein. Specifically, when a substrate for such a tag enzyme protein (e.g., glutathione for GST, or maltose for MBP) is fixed onto a surface, and a cofactor fused with the tag enzyme protein is brought into contact with the surface, a desired cofactor-bound surface can be formed through binding of the substrate to the enzyme.

A characteristic feature of the aforementioned system employing avidin-biotin binding resides in that different cofactors can be bound, via biotin, to an avidin-immobilized surface without fusion of the cofactors with tag proteins; i.e., the system is more convenient.

[Detection of Target Substance]

The present detection method is mainly intended to determine whether or not a component of a test sample (generally a sample containing a target substance candidate) is a target substance.

The target substance is a substance having any effect on a nuclear receptor; specifically, an agonist, an antagonist, or a modulator. The target substance may be a synthetic product or a naturally occurring substance.

The present detection method employs, as a detection indicator, a change in degree of binding between a nuclear receptor protein and a specific cofactor, which is based on that, when the nuclear protein binds to a specific target substance, the nuclear receptor binds to the cofactor immobilized on a "surface," and thus an agonist-bound nuclear receptor remains on the surface. Therefore, preferably, there is employed a label which enables a nuclear receptor protein bound to an immobilized cofactor to be detected.

Such a label may be, for example, a color-developing enzyme, a fluorescent dye, or an isotope. Preferably, there is employed a labeled antibody prepared by labeling an anti-nuclear receptor protein antibody with such a label. Particularly, a color-developing enzyme (e.g., peroxidase) is preferably employed as such a label.

The labeled antibody may recognize a nuclear receptor protein per se as an antigenic determinant. However, as described above, in the case where a fusion protein is produced through fusion of a nuclear receptor protein with a tag protein, and the tag protein is employed as an antigenic determinant, when existing anti-tag protein labeled antibodies [e.g., commercially available anti-GST tag antibody and anti-His tag antibody (both are products of Cosmo Bio Co., Ltd.)] are employed, a nuclear receptor to which such a labeled antibody has been bound can be readily detected, without production of antibodies to different individual nuclear receptor proteins. Thus, when a fusion protein is produced through fusion of a nuclear receptor protein with a tag protein, a desired detection system can be rapidly established. In addition, when tag proteins which are fused with a plurality of nuclear receptor proteins are grouped in advance in accordance with the nuclear receptor proteins, different combinations of target substances, nuclear receptors, and cofactors can be efficiently assayed as a whole.

In the present detection method, in the case where a target substance is an agonist for a nuclear receptor, for example, a nuclear receptor protein and a test sample are exposed to a surface on which a cofactor serving as a coactivator has been immobilized, and binding of the nuclear receptor protein to the immobilized coactivator—which occurs as a result of induction of structural change of the nuclear receptor protein through binding of an agonist contained in the test sample to the receptor protein—is detected, whereby a target agonist can be detected. This agonist can be detected by detecting an increase in amount of the nuclear receptor protein bound to the aforementioned surface as an increase in label signal intensity (i.e., a change in intensity as measured on the label of a labeled antibody) in the above-described manner. In such an agonist detection mode, when no increase in label signal intensity is observed, the test sample is found to contain no target agonist.

In the case where a target substance is an agonist, and a cofactor serving as a corepressor is employed, for example, a known antagonist for a nuclear receptor is bound to the nuclear receptor, to thereby provide a corepressor-nuclear receptor-label binding on a surface in advance, and to achieve a state where the surface is labeled. Subsequently, a test sample in which a target substance is an agonist is exposed to the surface, to thereby cause an agonist candidate to compete with the antagonist which has been bound to the nuclear receptor, whereby a target agonist can be detected on the basis of a reduction in label signal intensity due to the presence of the antagonist. Specifically, when the test sample contains a target agonist, the agonist is substituted for the antagonist which has been bound to the nuclear receptor protein, and thus the nuclear receptor protein, whose structure is changed into an unbound structure, dissociates from the immobilized cofactor serving as a corepressor, leading to a reduction in label signal intensity in the reaction system. In contrast, when substantially no reduction in label signal intensity is observed, the agonist candidate is actually an antagonist or a substance having no ability to bind to the nuclear receptor employed.

In the present detection method, in the case where a target substance is an antagonist for a nuclear receptor, for example, a nuclear receptor protein and a test sample are exposed to a surface on which a cofactor serving as a corepressor has been immobilized, and binding of the nuclear receptor protein to the immobilized corepressor—which occurs as a result of induction of structural change of the nuclear receptor protein through binding of an antagonist contained in the test sample to the receptor protein—is detected, whereby a target antagonist can be detected. This antagonist detection can be performed by detecting an increase in amount of the nuclear receptor protein bound to the aforementioned surface as an increase in label signal intensity in the above-described manner. In such an antagonist detection mode, when no increase in label signal intensity is observed, the test sample is found to contain no target antagonist.

In the case where a target substance is an antagonist, and a cofactor serving as a coactivator is employed, for example, a known agonist for a nuclear receptor is bound to the nuclear receptor, to thereby provide a coactivator-nuclear receptor-label binding on a surface in advance, and to achieve a state where the surface is labeled. Subsequently, a test sample in which a target substance is an antagonist is exposed to the surface, to thereby cause an antagonist candidate to compete with the agonist which has been bound to the nuclear receptor, whereby a target antagonist can be detected on the basis of a reduction in label signal intensity due to the presence of the agonist. Specifically, when the test sample contains a target antagonist, the antagonist is substituted for the agonist which has been bound to the nuclear receptor protein, and thus the nuclear receptor protein, whose structure is changed into an unbound structure, dissociates from the immobilized cofactor serving as a coactivator, leading to a reduction in label signal intensity in the reaction system. In contrast, when substantially no reduction in label signal intensity is observed, the antagonist candidate is actually an agonist or a substance having no ability to bind to the nuclear receptor employed.

Thus, when the type of a cofactor which is immobilized on a plate is changed to a coactivator or a corepressor in accordance with use, the agonistic or antagonistic effect of a target substance can be evaluated in detail.

BRIEF DESCRIPTION OF THE DRAWINGS

FIG. 5 is a flow sheet showing a step of establishing a detection system in the present detection method and the existing method, and shows a difference in operational efficiency between these methods.

FIG. 8 shows that E2 can be assayed by an ER-α assay system, regardless of the type of a coactivator (SRC1 or TIF2).

FIGS. 9A to 9E show that the present detection method can assay agonists for the following nuclear receptors: vitamin D receptor, peroxisome proliferator-activated receptor γ, liver X receptor α, liver X receptor β, and farnesol X receptor.

BEST MODE FOR CARRYING OUT THE INVENTION

Figure 1:
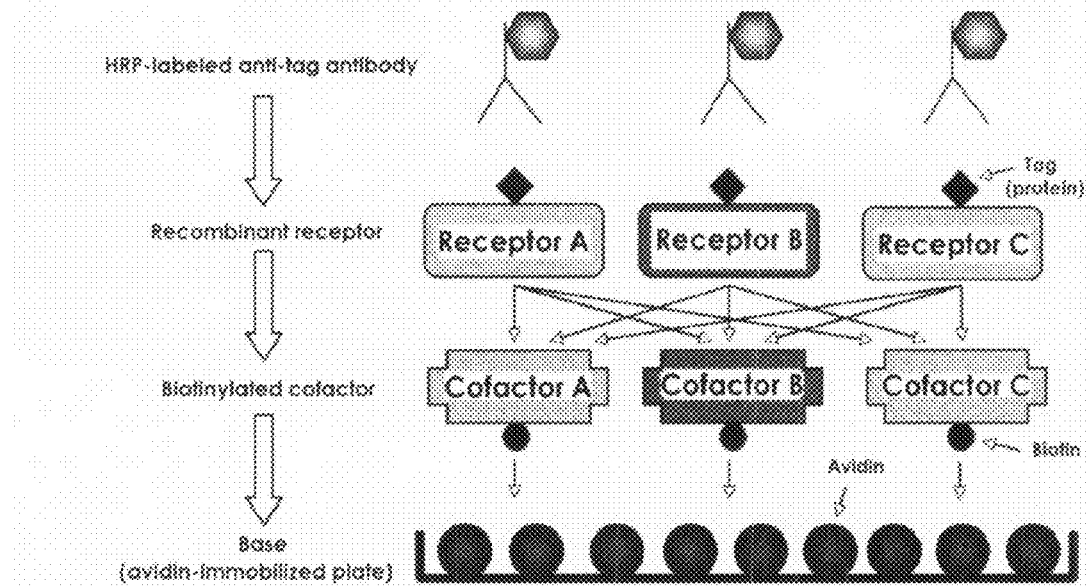
FIG. 1 is a schematic representation showing one of the best modes of the present detection method.

FIG. 1 is a schematic representation showing one of the best modes of the present detection method. As shown in FIG. 1, firstly, when a ligand (target substance) binds to a nuclear receptor, the nuclear receptor undergoes structural change. The structural change is recognized by a cofactor immobilized on a plate, whereby a ligand-receptor-cofactor complex is formed, and the complex binds to a plate surface. The thus-bound complex is reacted with an HRP-labeled antibody specific to a recombinant protein produced through fusion of the nuclear receptor protein with a tag protein, followed by color development of the resultant product by use of a detection reagent. Characteristics of a test sample can be detected on the basis of a change in colorimetric intensity.

In the present invention, avidin is immobilized on the plate surface in advance, and biotin is bound to the cofactor. Therefore, cofactor replacement can be easily performed as compared with the case where a cofactor is immobilized directly on a plate. In addition, since an antibody specific to the tag protein fused with the nuclear receptor protein is employed, time and labor are not required for producing antibodies specific to respective receptors, and any receptor-cofactor combination assay system can be rapidly established.

Figure 2:
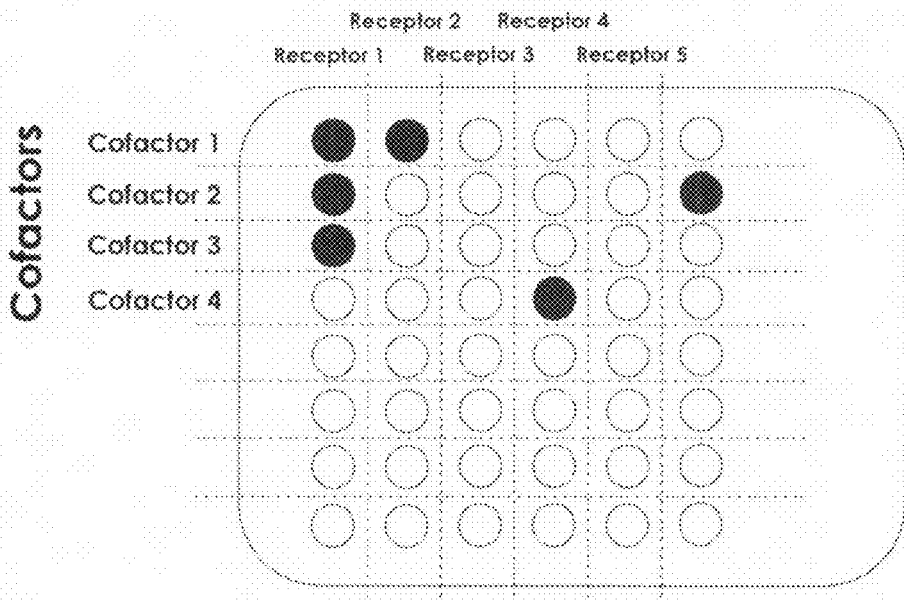
FIG. 2 is a schematic representation showing an embodiment of the present detection method, which is established on a microwell plate employing combinations of different nuclear receptors and cofactors.

When simultaneous detection is performed on combinations of a plurality of nuclear receptors and a plurality of cofactors in wells of a microwell plate (FIG. 2), difference in response of a test sample to the nuclear receptor-cofactor combinations can be rapidly detected, and useful data in relation to evaluation of the effect of the sample on living organisms can be obtained.

EXAMPLES

The present invention will next be specifically described by way of examples, which should not be construed as limiting the invention thereto.

[Preparation of Reagent]

Reagents employed in Examples were prepared in the following procedure.

(1) Color-Developing Reagent:

A color-developing reagent was prepared by dissolving tetramethylbenzidine (hereinafter abbreviated as "TMB") in an acetate buffer (pH 6.5) at a concentration of 5.5 mM.

(2) Washing Buffer:

A washing buffer was prepared by adding Tween 20 to 0.2 M phosphate buffered saline (hereinafter abbreviated as "PBS") at a concentration of 0.05%.

Referential Example 1

Preparation of Human Estrogen Receptor α-GST Fusion Protein and Human Estrogen Receptor β-GST Fusion Protein A human estrogen receptor α-GST fusion protein (hereinafter abbreviated as "ER-α") and a human estrogen receptor β-GST fusion protein (hereinafter abbreviated as "ER-β") were prepared through a known method (Cowly, S. M., et al., J. Biochem., 272, 19858-19862 (1997)). In brief, these fusion proteins were prepared in the following procedure.

A gene encoding a ligand-binding region of human estrogen receptor α or β was obtained through RT-PCR using, as a template, RNA extracted from a culture supernatant of human breast cancer cells (MCF-7) by use of a commercially available RNA extraction kit (Isogen, product of Nippon Gene Co., Ltd.). The resultant PCR product was inserted into an *Escherichia coli* expression vector (pGEX, product of Amersham Bioscience) between sites cleaved by restriction enzymes (EcoRI and BamHI), followed by introduction into *Escherichia coli* BL21. Culturing was performed in an LB medium at 37° C. until OD600 reached about 0.5, followed by IPTG induction, and culturing at room temperature for five hours. *Escherichia coli* cells collected through centrifugation were suspended in an ER buffer (40 mM Tris, 5 mM EDTA-2Na, 0.5% w/v Triton X-100, 0.05% NaN3, pH 7.5), followed by sonication on ice. After centrifugation, the thus-collected supernatant was applied to a glutathione-Sepharose column (GSTrap FF Prepack Column, product of Amersham Bioscience) equilibrated in advance with a binding buffer (10 mM Na2HPO4, 1.8 mM KH2PO4, 140 mM NaCl, pH 7.3), followed by washing with the binding buffer, and elution with an elution buffer (50 mM Tris, 10 mM non-reducing glutathione, pH 8.0). The thus-obtained ER-α or ER-β was stored at −80° C. until the time immediately before use thereof.

Referential Example 2

Preparation of Other Nuclear Receptor-GST Fusion Proteins

In a manner similar to that of Referential Example 1, there were expressed a rat vitamin D receptor-GST fusion protein (hereinafter abbreviated as "rVDR"), a human peroxisome proliferator-activated receptor γ-GST fusion protein (hereinafter abbreviated as "PPAR-γ"), a human liver X receptor α-GST fusion protein (hereinafter abbreviated as "LXR-α"), a human liver X receptor β-GST fusion protein (hereinafter abbreviated as "LXR-β"), and a human farnesol X receptor-GST fusion protein (hereinafter abbreviated as "FXR").

A gene encoding a ligand-binding region of each of the receptors was obtained from a commercially available cDNA library through a customary method. All the employed cDNA libraries and cDNA clones were purchased from OriGene Technologies, Inc. (USA).

Referential Example 3

Preparation of Biotinylated Coactivator SRC1

A biotinylated coactivator peptide targeting SRC1, which is a cofactor serving as a coactivator, was prepared in the follow procedure.

A peptide consisting of 15 amino acids (LTERHKILHR-LLQEG), which correspond to Nos. 683 to 697 of the amino acid sequence of SRC1, was synthesized by means of Shimadzu SynProPep, PSSM-8, and was biotinylated by means of Biotinylation kit (PIERCE).

Referential Example 4

Preparation of Biotinylated Coactivator TIF2

A biotinylated coactivator peptide targeting TIF2, which is a cofactor serving as a coactivator, was prepared in the following procedure.

A peptide consisting of 15 amino acids (LKEKHKILHR-LLQDS), which correspond to Nos. 683 to 697 of the amino acid sequence of TIF2, was synthesized by means of Shimadzu SynProPep, PSSM-8, and was biotinylated by means of Biotinylation kit (PIERCE).

Referential Example 5

Plate Preparation

Avidin (product of Wako Pure Chemical Industries, Ltd.) was diluted with 0.1 M NaHCO$_3$ (pH 8.4) to 10 μg/mL, and the thus-diluted avidin was added to a 96-well microwell plate (MaxiSorp, product of Nunc) (100 μL/well), followed by allowing the plate to stand still at 4° C. for 16 to 24 hours. Thereafter, each of the wells was washed with PBS (pH 7.4) three times, and a blocking buffer (PBS containing 1% bovine serum albumin (hereinafter abbreviated as "BSA"), pH 7.4) was dispensed into the plate (200 μL/well), followed by allowing the plate to stand still at 4° C. for 16 hours or more, to thereby prepare an avidin plate. The avidin plate was stored at 4° C. until use.

Example 1

Evaluation of Effects of the Present Invention

Through comparison with an existing method, effects of the present invention were evaluated in terms of operational efficiency in establishing an assay system (time required for operation, and the number of plates prepared per unit material). The results are shown hereinbelow.

(1) Existing Method

An ER-α preparation (10 mL) was purified from an ER-α cell culture (1 L) by use of glutathione-Sepharose 4B gel (product of Amersham Bioscience). There was established, as an existing method, an assay system in which an ER-α preparation is immobilized on a 96-well microwell plate. ER-α was appropriately diluted with PBS by a factor of 1/1, 1/2, 1/4, or 1/8, and the thus-diluted ER-α was dispensed into the plate (50 μL/well). The ER-α-dispensed plate was allowed to stand still at 4° C. for 16 hours or more for immobilization of ER-α. Thereafter, the plate was subjected to a blocking treatment by use of PBS containing 1% BSA at 4° C. for 16 hours or more. The ER-α-immobilized plate was subjected to activity assay by use, as a sample, of a liquid mixture of a 17 β-estradiol standard (E2) (concentration: 10 nM, 1 nM, 0.1 nM, or 0 nM), a biotinylated coactivator SRC1 (0.1 μg/mL, dissolved in dimethyl sulfoxide (hereinafter abbreviated as "DMSO")), and HRP-labeled avidin (1/200 diluted solution, AMEDEX, product of Amersham Bioscience). Biotinylated SRC1, HRP-labeled avidin, and PBS were mixed in proportions of 1:1:98 in advance, to thereby prepare a solution (solution A). The E2 standard and the solution A were mixed at a ratio of 5:95, and the mixture was dispensed into the ER-α-immobilized plate (100 μL/well). After reaction with shaking at room temperature for one hour, the plate was washed with a washing buffer. After washing of the plate, a color-developing reagent was added to the plate (100 μL/well), and the plate was allowed to stand still for 10 minutes for color development reaction. Color development reaction was stopped by use of 1 N sulfuric acid, followed by measurement at a wavelength of 450 nm by means of a plate reader.

(2) The Present Detection Method

In a manner similar to that of the aforementioned existing method, a purified ER-α product (10 mL) was prepared from an ER-α cell culture (1 L). By use of this product, the amount of an assay reagent prepared was examined as described hereinbelow. Avidin was immobilized on a plate in advance, and a biotinylated coactivator SRC1 (0.01 mg/mL, dissolved in DMSO) was prepared into a solution (final concentration: 0.01 μL/mL) by use of a washing buffer. The thus-prepared solution was dispensed into the plate (100 μL/well), followed by impregnation for one hour, to thereby prepare an SRC1-bound plate. Subsequently, an ER-α solution prepared by appropriately diluting the ER-α product with PBS by a factor of 1/10, 1/20, 1/40, 1/60, 1/80, or 1/120 and an E2 standard liquid were mixed at a ratio of 95:5, and the mixture was dispensed into the plate (100 μL/well). After reaction with shaking for one hour, the plate was washed with a washing buffer, and an HRP-labeled anti-GST antibody solution prepared by diluting the antibody with a washing buffer by a factor of 1/40,000 was dispensed into the plate (100 μL/well), followed by reaction with shaking for one hour. After reaction, the plate was washed with a washing buffer; a color-developing reagent was added to the plate (100 μL/well); and the plate was allowed to stand still for 10 minutes for color development reaction. Color development reaction was stopped by use of 1 N sulfuric acid, followed by measurement at a wavelength of 450 nm by means of a plate reader.

Figure 3:
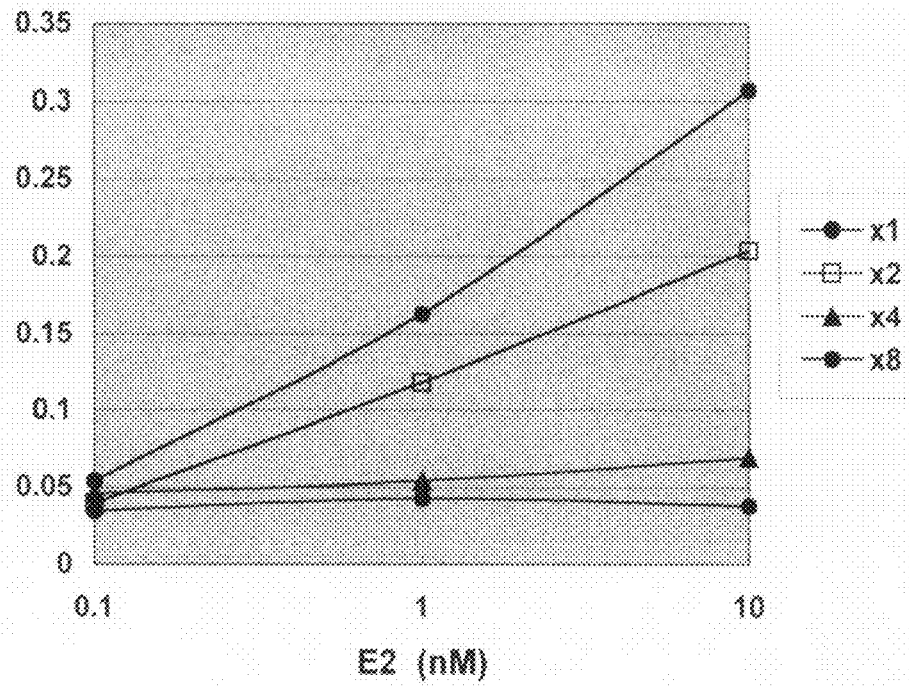
FIG. 3 is a graph showing the relation between ER activity and concentration of an ER-α preparation purified from an *Escherichia coli* culture (1 L), the relation being obtained by an existing method (receptor-immobilized plate).

FIG. 3 shows data of activity assay by use of the plate prepared through the existing method, on which an ER-α preparation purified from an ER-α culture (1 L) was immobilized at an appropriate concentration. These data indicated that when ER-α is immobilized, in order to attain sufficient activity, the purified ER-α preparation must be used as it is, or must be concentrated before use. The amount of an assay reagent prepared is roughly estimated as follow. The amount of ER-α which is required as an assay reagent and which is immobilized on one plate is about 10 mL, which is calculated on the basis of 100 μL/well. Therefore, the amount of the assay reagent prepared from a 1-L ER-α culture corresponds to one 96-well microwell plate or less.

Figure 4:
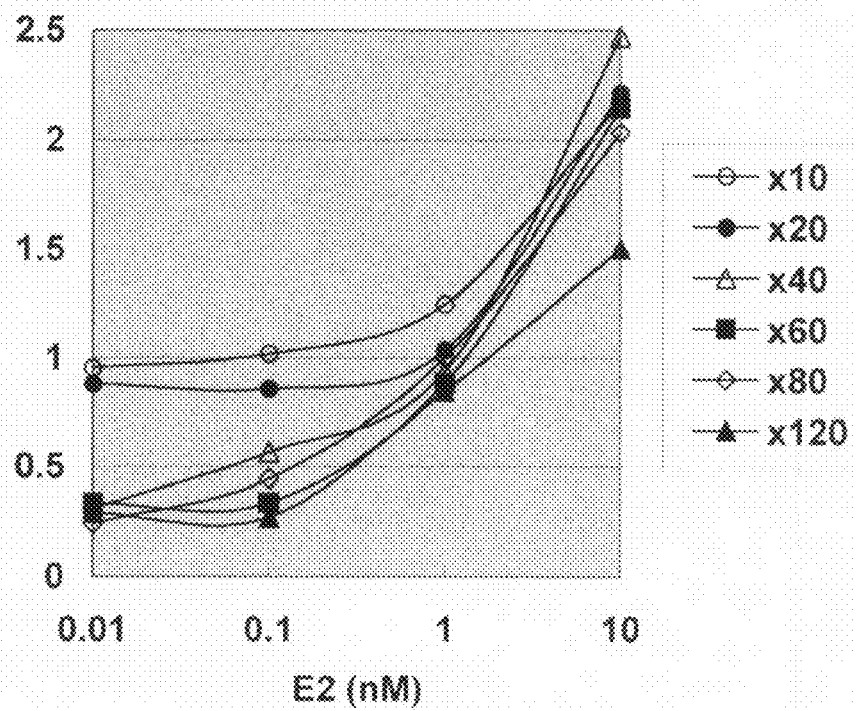
FIG. 4 is a graph showing the relation between ER activity and concentration of an ER-α preparation purified from a culture (1 L), the relation being obtained by the present detection method.

FIG. 4 shows data of the amount of ER-α required for the present detection method. These data indicated that when a detection system is established on the basis of the present detection method, 60-fold diluted ER-α is enough to attain sufficient activity. The amount of ER-α required as an assay reagent for one microwell plate is 12 mL/kit. Therefore, when 60-fold diluted ER-α is employed, the number of plates which can be prepared by use of a 1-L ER-α culture is estimated to be 50 on the basis of the following calculations (60×10 mL=600 mL, and 600/12=50).

When the same amount of an assay reagent is prepared through the aforementioned existing method, the required amount of an ER-α culture is at least 50 L. As shown in FIG. 5, under the assumption that a 1-L ER-α culture is one unit for kit production, 50 plates can be produced in a week through the present detection method. In contrast, in the existing method, two weeks are required for production of five plates. When, as in the case of the novel method, an assay reagent for 50 kits is prepared through the existing method according to this process flow, at least two months are required for the preparation.

Test Example 1

Assay of Ligand Using Coactivator SRC1-Bound Plate

Figure 6A:
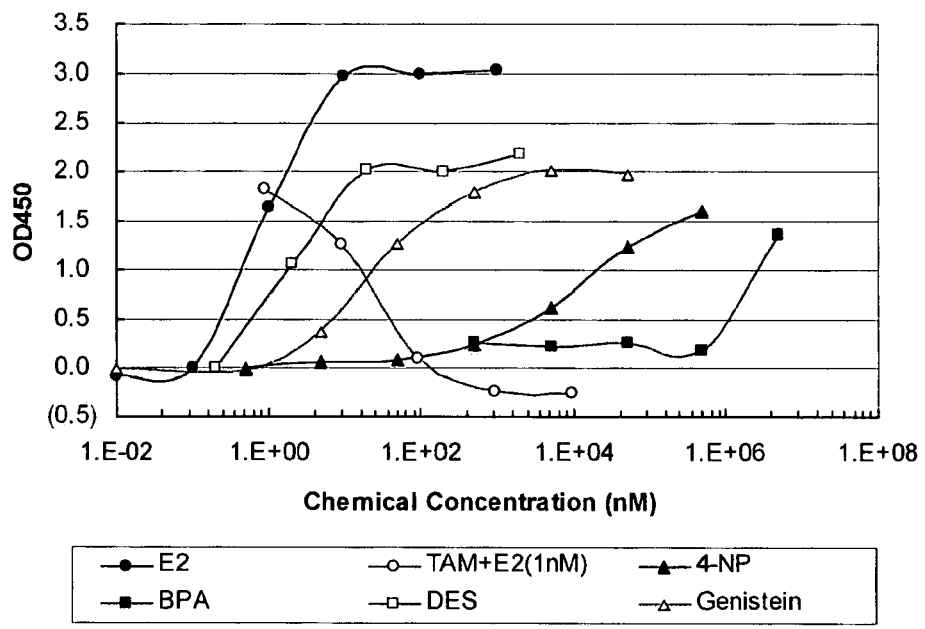
FIGS. 6A and 6B are graphs showing the results of assay of different ligands for estrogen receptors α and β using a coactivator SRC1-bound plate in the present detection method.
Figure 6B:
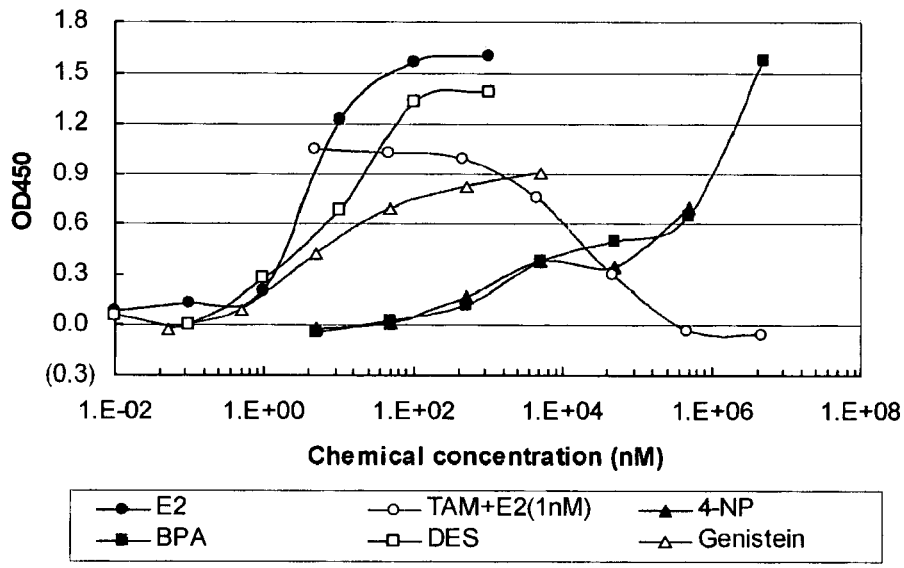

A coactivator SRC1 was immobilized on an avidin plate prepared in Referential Example 5, and two assay systems employing nuclear receptors were established; i.e., an assay system employing a nuclear receptor (ER-α) obtained through the present detection method described in Example 1, and an assay system in which the receptor ER-α was replaced by ER-β. An HRP-labeled anti-GST antibody was employed for assay. As shown in FIGS. 6A and 6B, in each of the assay systems employing the nuclear receptors, an increase in OD was observed for the cases of 17 β-estradiol (E2), bisphenol A (BPA), diethylstilbestrol (DES), nonylphenol (4-NP), and genistein, which are agonists. When tamoxifen (TAM) (i.e., an antagonist) was mixed with a predetermined concentration of E2, followed by assay, a reduction in OD was observed in a TAM dose-dependent manner. This indicates that the present detection method can discriminate between an agonist and an antagonist for a nuclear receptor.

Test Example 2

Evaluation of Estrogen Receptor Selectivity

Figure 7A:
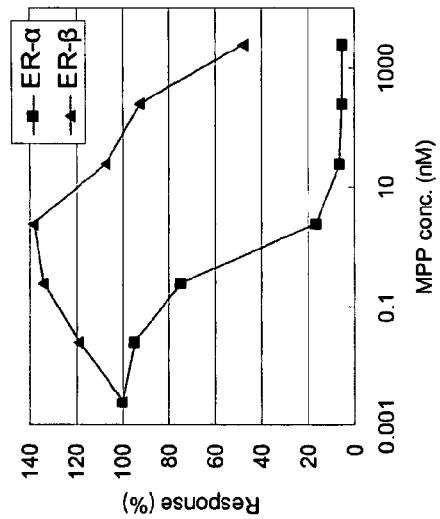
FIGS. 7A to 7C show the results of assay of a receptor selective agonist and antagonist for estrogen receptors α and β using a coactivator SRC1-bound plate in the present detection method, indicating that the present detection method can evaluate such an agonist or antagonist.
Figure 7B:
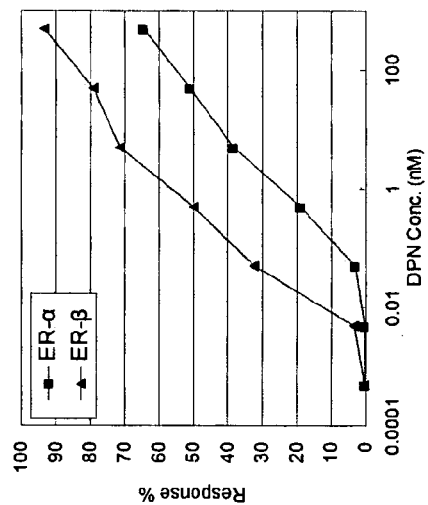
Figure 7C:
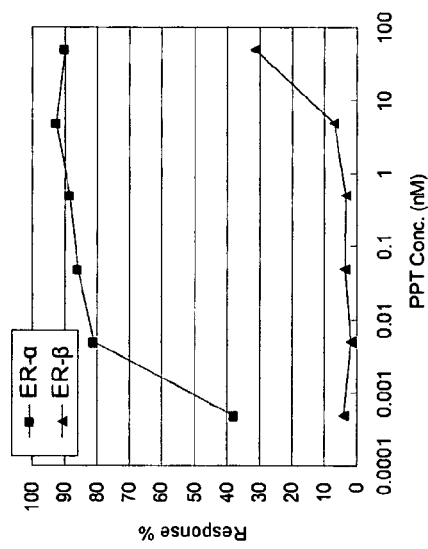

Known estrogen receptor-α selective agonist, estrogen receptor-β selective agonist, and estrogen-α selective antagonist were evaluated by use of the systems employing ER-α and ER-β established in Test Example 1. As shown in FIGS. 7A to 7C (each vertical axis corresponds to absorbance relative to that of E2), propyl-pyrazole-triol (PPT), which is an ER-α selective agonist, was found to exhibit an agonistic effect greater on ER-α than on ER-β. Meanwhile, diarylpropionitrile (DPN), which is an ER-β selective agonist, was found to exhibit a strong agonistic effect on ER-β. MPP dihydrochloride (MPP), which is an ER-α selective antagonist, was mixed with a predetermined concentration of E2, and the antagonistic effect of MPP was evaluated. As a result, MPP was found to exhibit an antagonistic effect greater on ER-α than on ER-β.

These results are similar to those of evaluation of the aforementioned ligands through the cell-based reporter gene assay reported in W. R. Harrington, et al., Mol. And Cell. Endcri. 206 (2003) 13-22. That is, the detection method was found to be more convenient than the reporter gene assay, and to enable receptor selectivity of a ligand to be evaluated.

Test Example 3

Examination of Estrogen Receptor Binding Test Using Coactivator TIF2-Bound Plate Subsequently, in place of a coactivator SRC1, a biotinylated coactivator TIF2 was bound to an avidin plate, and an estrogen receptor (ER-α) test was established. The method and constitution of an assay system are similar to those described in Test Example 1, except for replacement of the coactivator. As shown in FIG. 8, both the SRC1-bound plate and the TIF2-bound plate were found to enable E2 to be assayed by the mediation of ER-α.

Test Example 4

Examination of Applicability of the Present Detection Method to Various Nuclear Receptors In the detection method, rVDR, PPAR-γ, LXR-α, LXR-β, or FXR was employed as a nuclear receptor-GST fusion protein, and an agonist for each of the nuclear receptors was assayed in a manner similar to that of Test Example 1. There were employed the following agonists: 1α,25-dihydroxyvitamin D (VD3) for rVDR; troglitazone (TRO) for PPAR-γ; TO-901317 (TO) for LXR-α and LXR-β; and chenodeoxycholic acid (CDCA) for FXR. FIGS. 9A to 9E show the results of assay of the agonists for the respective nuclear receptors. In each of the nuclear receptors, OD was increased in a manner dependent on the dose of the corresponding agonist. That is, the present detection method was found to be readily applicable to other nuclear receptors such as vitamin D receptor, peroxisome proliferator-activated receptor γ, liver X receptor α, liver X receptor β, and farnesol X receptor.

INDUSTRIAL APPLICABILITY

According to the present invention, there is provided means for detecting a living-body-related substance, which means employs a nuclear receptor-cofactor system, exhibits high detection sensitivity, provides a convenient detection process, and realizes efficient establishment of a detection system.

The invention claimed is:

1. A detection method comprising:
   exposing, to a surface to which a cofactor has been bound, said surface being a surface of a well of a microwell plate, and said binding between the surface and the cofactor being maintained by avidin-biotin binding between avidin or streptavidin immobilized on the surface and biotin bound to the cofactor, a nuclear receptor protein serving as a counterpart of the cofactor and a test sample; a tag protein being bound to said nuclear receptor protein;
   detecting a change in degree of binding between the nuclear receptor protein and the cofactor as a change in intensity as measured on the label of a labeled antibody which can bind to the tag protein; and
   detecting a substance which is contained in the test sample and which binds to the nuclear receptor, on the basis of the change in intensity as measured on the label of a labeled antibody which can bind to the tag protein,
   wherein the method employs two or more nuclear receptor proteins and cofactors serving as counterparts of the respective proteins, and the method is performed in different respective wells of a single microwell plate to thereby collectively detect substances which are contained in a test sample and which bind to the two or more nuclear receptors.

2. The detection method according to claim 1, wherein an agonist or antagonist for the nuclear receptor, which is contained in the test sample, is detected on the basis of an increase in degree of binding between the nuclear receptor protein and the cofactor.

3. The detection method according to claim 1, wherein an antagonist or agonist for the nuclear receptor, which is contained in the test sample, is detected on the basis of a reduction in degree of binding between the nuclear receptor protein and the cofactor.

4. The detection method according to claim 1, wherein the label of the antibody is a peroxidase.

5. The detection method according to claim 4, wherein the nuclear receptor protein and/or the cofactor is a recombinant protein.

6. The detection method according to claim 5, wherein the nuclear receptor protein is one or more nuclear receptor proteins selected from among estrogen receptor α, estrogen receptor β, androgen receptor, progesterone receptor, glucocorticoid receptor, mineralcorticoid receptor, retinoic acid receptor α, retinoic acid receptor β, retinoic acid receptor γ, thyroid hormone receptor α, thyroid hormone receptor β, vitamin D receptor, retinoid X receptor α, retinoid X receptor β, retinoid X receptor γ, peroxisome proliferator-activated receptor α, peroxisome proliferator-activated receptor γ, peroxisome proliferator-activated receptor δ, liver X receptor α, liver X receptor β, farnesol X receptor, steroid and xenobiotic receptor, constitutive androstane receptor, Rev-Erb A receptor α, Rev-Erb A receptor β, RAR-related orphan receptor α, RAR-related orphan receptor β, RAR-related orphan receptor γ, hepatocyte nuclear factor 4α, hepatocyte nuclear factor 4γ, testicular orphan receptor 2, testicular orphan receptor 4, chicken ovalbumin upstream promoter transcription factor I, chicken ovalbumin upstream promoter transcription factor II, chicken ovalbumin upstream promoter transcription factor γ, estrogen-related receptor α, estrogen-related receptor β, estrogen-related receptor γ, nerve growth factor-inducible gene Bα, nerve growth factor-inducible gene Bβ, nerve growth factor-inducible gene Bγ, germ cell nuclear factor, steroidogenic factor 1, liver receptor homologous protein, photoreceptor cell-specific nuclear receptor, *Drosophila tailless* gene receptor human homologue, small heterodimer partner protein, and dosage-sensitive sex reversal-AHC critical region on the X chromosome gene 1.

* * * * *